United States Patent [19]

Cross et al.

[11] 4,087,612

[45] May 2, 1978

[54] PROCESS FOR PREPARING PYRAZOLIDINES COMPOUNDS

[75] Inventors: Barrington Cross, Rocky Hill; Charles Paul Grasso, East Windsor; Bryant Leonidas Walworth, Pennington, all of N.J.

[73] Assignee: American Cyanamid Company, Stamford, Conn.

[21] Appl. No.: 751,301

[22] Filed: Dec. 16, 1976

Related U.S. Application Data

[60] Continuation of Ser. No. 624,154, Oct. 20, 1975, abandoned, which is a division of Ser. No. 526,358, Nov. 22, 1974, Pat. No. 3,948,936.

[51] Int. Cl.² .......................................... C07D 231/04

[52] U.S. Cl. ........................................ 548/356; 71/92; 548/373; 548/379

[58] Field of Search ................... 260/310 D; 526/358; 548/356

[56] References Cited

U.S. PATENT DOCUMENTS

| | | | |
|---|---|---|---|
| 3,404,157 | 10/1968 | McEvoy | 260/310 R |
| 3,925,408 | 12/1975 | Cross | 260/311 |

*Primary Examiner*—Natalie Trousof
*Assistant Examiner*—Jane T. Fan
*Attorney, Agent, or Firm*—Harry H. Kline

[57] ABSTRACT

This invention relates to herbicidal pyrazolidine compounds, to a method of preparing the same by the reduction of either a pyrazolium or a pyrazolinium salt.

4 Claims, No Drawings

PROCESS FOR PREPARING PYRAZOLIDINES COMPOUNDS

This application is a continuation of our copending application, Ser. No. 624,154, filed on Oct. 20, 1975, now abandoned which in turn is a divisional of Ser. No. 526,358, filed on Nov. 22, 1974, now U.S. Pat. No. 3,948,936, issued on Apr. 6, 1976.

The present invention relates to pyrazolidine compounds and the acid salts thereof which are represented by the formulas:

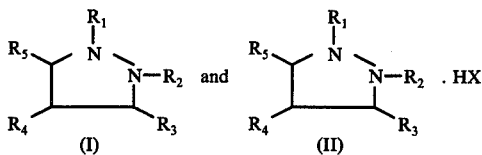

wherein $R_1$ and $R_2$ each represent alkyl $C_1$–$C_4$; $R_3$ and $R_5$ each represent a member selected from the group consisting of alkyl $C_2$–$C_{12}$, cycloalkyl $C_3$–$C_7$, methylcycloalkyl $C_4$–$C_8$, cycloalkenyl $C_3$–$C_7$, methylcycloalkenyl $C_4$–$C_8$, cycloalkylmethyl $C_4$–$C_8$, benzyl and

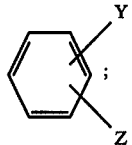

Y and Z each represent a member selected from the group consisting of hydrogen, halogen, alkyl $C_1$–$C_4$, alkoxyl $C_1$–$C_4$, methylthio, methylsulfonyl, carboxy, carboalkoxy, carboxamido and cyano; $R_4$ represents a member selected from the group consisting of hydrogen, alkyl $C_1$–$C_{10}$, alkoxy $C_1$–$C_4$ and alkylthio $C_1$–$C_4$, provided that when $R_4$ is hydrogen or methyl, at least one of $R_3$ and $R_5$ is a member other than unsubstituted phenyl; and HX represents an acid, preferably selected from the group consisting of HCl, HBr, HI, HNO$_3$, H$_3$PO$_4$, H$_2$SO$_4$, HClO$_4$, HBF$_4$ and

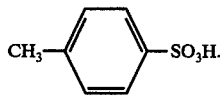

The invention also relates to a process for preparing the aforementioned.

As preferred pyrazolidine compounds, these are depicted by formulas (I) and (II) above, wherein $R_1$ and $R_2$ are each methyl; $R_3$ and $R_5$ are each cycloalkyl $C_3$–$C_7$ or

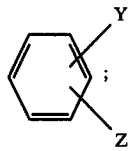

$R_4$ is hydrogen, alkyl $C_1$–$C_3$ or alkoxy $C_1$–$C_3$, provided that when $R_4$ is hydrogen or methyl, one of $R_3$ and $R_5$ is a member other than unsubstituted phenyl; Y and Z each represent hydrogen, halogen (and preferably fluoro), methyl, methoxy, carboxy, CO$_2$CH$_3$, CONH$_2$ and CONHCH$_3$; and HX is an inorganic acid selected from those mentioned above.

A still more preferred embodiment of this invention relates to pyrazolidine compounds depicted by formulas (I) and (II) shown above, wherein $R_1$ and $R_2$ are each methyl; $R_3$ is cyclohexyl, o-, m- or p-fluorophenyl, o-, m- or p-methylphenyl or o-carboxyphenyl; $R_5$ is cyclohexyl, phenyl, o-, m- or p-fluorophenyl, or o-, m- or p-methylphenyl; and $R_4$ is hydrogen, methyl, n-propyl, methoxy or n-propoxy; and in formula (II) compounds, HX is HI, HCl, HBr, HNO$_3$ or H$_2$SO$_4$.

The above-identified pyrazolidine compounds, which are represented by formulas (I) and (II), can be prepared as the "cis" and the "trans" isomers. Both isomeric forms of the compounds are biologically active; however, the "cis" isomers are the more active of the two. Mixed isomer compositions are, of course, also biologically active.

The above-said compounds and the method for controlling undesirable plant species, especially wild oats and broadleaf weeds, are considered as an integral part of the present invention.

The herbicidal method may be carried out with the above-defined pyrazolidines or salts thereof. Alternatively, they may be carried out with similar pyrazolidines or pyrazolidine salts, wherein $R_4$ is hydrogen or methyl and $R_3$ and $R_5$ are each phenyl.

Preferred compounds for use as a herbicide are represented by formulas (I) and (II) above, wherein $R_1$ and $R_2$ are each methyl; $R_4$ is hydrogen, methyl, n-propyl, methoxy or n-propoxy; $R_3$ and $R_5$ each represent a member selected from the group consisting of cycloalkyl $C_3$–$C_7$ and

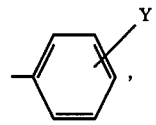

where Y is hydrogen, methyl or fluoro; and HX represents an acid as hereinabove defined, preferably HCl, HBr, HI, HNO$_3$ or H$_2$SO$_4$.

It is to be noted that, although, the pyrazolidines and pyrazolidine salts of this invention appear to be similar to pyrazolium and pyrazolinium compounds, it will be recognized that latter-named compounds are quaternary salts. Such compounds are ionic and generally water soluble. Contrariwise, the pyrazolidine (I) of the present invention are not salts; nor are they quaternary compounds. They are water-insoluble. The pyrazolidine (II) compounds are, of course, salts; however, like the (I) pyrazolidines, they are not quaternary compounds. This is because quaternary compounds are obtained with a positive charge on a nitrogen atom and a carbon atom attached to the nitrogen, whereas the salt is obtained by protonation of the nitrogen which may or may not have an alkyl group attached thereto. A salt and a quaternary moiety may be illustrated as follows:

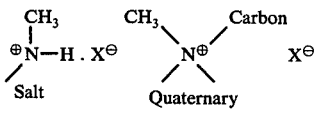

Additionally, the action of a base on an HX salt of an amine will regenerate the amine, i.e. a pyrazolidine, whereas, the action of a base upon a pyrazolium compound merely changes the counterion $X^\ominus$ to $OH^\ominus$.

The pyrazolidines (I) are nonionic, lipophilic molecules which are found to be effective postemergence herbicidal agents. These compounds are somewhat similar in postemergence herbicidal properties to the ionic hydrophilic pyrazolium compounds, but surprisingly exhibit some useful agronomic advantages over said compounds. Particularly noteworthy is the wheat selectivity of the compounds of this invention, especially against certain wheat varieties as hereinbelow described.

In general, the pyrazolidines of this invention can be prepared by a reductive process. In this regard, a pyrazolium compound, hereinafter defined as formula (III), can be reduced in protonic solvents with an excess of sodium borohydride at temperatures ranging between room temperature and reflux temperature in a lower monohydric alcohol solvent, preferably isopropanol at 80° C. If desired, lithium aluminum hydride in an ether, such as tetrahydrofuran or diethyl ether may be substituted for sodium borohydride. Alternatively, milder sodium borohydride reducing conditions, such as room temperature, can also be employed for the reduction of 2-pyrazolinium compounds to pyrazolidines. Resultant pyrazolidines are readily separated from any unreacted starting material by virtue of their solubility in aprotic solvents, such as benzene or ethers. They are also soluble in chlorinated hydrocarbons. Most of the pyrazolidines so obtained are oils, which are characterized by gas liquid chromatography (glc) and nuclear magnetic resonance (nmr) as isomer mixtures, generally, in the range of 80 cis: 20 trans. Further characterization of the pyrazolidines is obtained by conversion to a salt using an aqueous acid, such as hydrochloric acid or hydriodic acid. In some cases, the salt precipitates out such as with perchloric or hydriodic acid, and the product is removed by filtration. Where an oil results, it can be readily, if desired, be converted to a solid. However, the salt can also be extracted from the aqueous acidic medium with chloroform, which upon evaporation yields the salt. Hydrochlorides, for instance, can be prepared by passing dry hydrogen chloride gas through an aprotic solvent such as an ethereal solution of the pyrazolidine, from which the hydrochloride salt precipitates out and is removed by filtration.

In general, separation of cis and trans pyrazolidines is accomplished by a dry column chromatography technique using Woelm Silica Gel prepared for dry chromatography as the packing and hexane-ether (80:20) as the eluant. The "trans" isomer runs somewhat faster than the "cis" isomer, which is the basis for the separation. The separation is confirmed by gas-liquid chromatography (glc) employing a mixed phase column. Alternatively, the pyrazolidines of Formula (I) can be readily obtained from chalcones by successive reaction with hydrazines, followed by sodium borohydride reduction or reductive alkylation as shown in the series of reactions below:

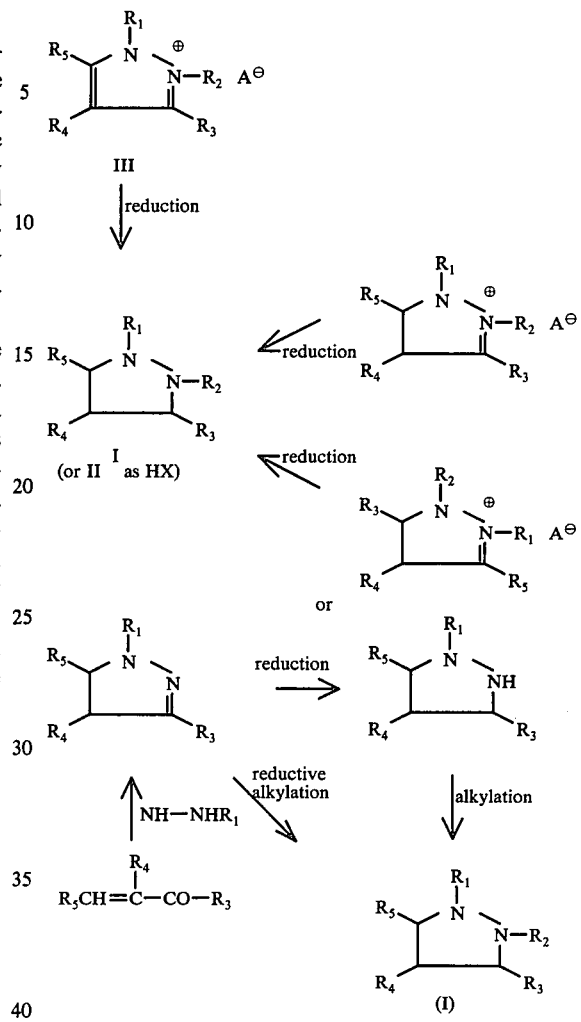

where $R_1$, $R_2$, $R_3$, $R_4$, $R_5$ are as defined above and A is an anion such as chloride, iodide, bromide, phosphate, sulfate, perchlorate, nitrate, p-toluenesulfonate, methyl sulfate or tetrafluoroborate.

As previously indicated, the compounds of this invention are effective herbicidal agents, and particularly useful for the control of wild oats. These compounds are highly selective in the presence of crops such as barley, wheat, rape, and the like, and can be used effectively for the control of undesirable plant species by application of a herbicidally effective amount of the active compound to the foliage of undesirable plants or to soil containing seeds of undesirable plants. It is found that about 0.56 kilogram per hectare (kg/ha) to 11.2 kilograms per hectare (kg/ha) of the pyrazolidine of pyrazolidine salt provide excellent control of wild oats and broadleaf weeds, such as lambsquaters, mustard and pigweed.

The compounds of the invention can be prepared as solid or liquid formulations including dusts, dust concentrates, emulsifiable concentrates and wettable powders. The two latter formulations are generally added to a spray tank at the site of use and diluted with water or other inexpensive solvent. Resultant dilute mixture is then applied as a liquid spray.

It is a good practice to prepare the formula (I) pyrazolidine free base as an emulsifiable concentrate and the formula (II) pyrazolidine salts as a wettable powder formulation. Dusts and dust concentrates of both are, of course, readily prepared with both formula (I) and formula (II) compounds.

Dusts are generally prepared by grinding together about 1% to 25% by weight of the active agent with from about 99% to 75% by weight of a solid diluent such as kaolin, attapulgite, talc, diatomaceous earth, wood flour, or the like. Dust concentrates are prepared in similar fashion, excepting that about 25% to 95%, by weight, of the active agent is ground with about 75% to 5%, by weight, of the diluent.

Wettable powders are prepared in the same manner as the dust concentrates, excepting that about 1% to 5%, by weight, of a dispersing agent such as the calcium salt of a polymerized alkyl aryl sulfonic acid, sodium lignosulfonate, or sodium salt of condensed naphthalene sulfonic acid, is blended with the mixture, and about 1% to 5% of a surfactant such as polyoxyethylated begetable oil, alkyl phenoxy polyoxyethylene ethanol, sodium alkyl naphthalene sulfonate, is also blended with the formulations.

The emulsifiable concentrate formulations can be prepared by dissolving about 25% to 75% by weight of the pyrazolidine free base in an aromatic solvent such as xylene, toluene or benzene, and adding thereto about 5% to 10% by weight of a nonionic, anionic or nonionic-anionic emulsifier. The thus prepared formulation is then readily dispersible in water and can be applied as a dilute spray.

For a fuller understanding, the following examples are presented. These are to be taken as illustrative and not as limitative of the invention.

EXAMPLE 1

Preparation of 1,2-Dimethyl-3,5-diphenylpyrazolidine

Sodium borohydride (19 g, 0.5 mole) is added portionwise to an isopropanol (1 liter) solution of 1,2-dimethyl-3,5-diphenylpyrazolium methyl sulfate (40.1 g, 0.25 mole). The reaction is allowed to stir at room temperature for 3 days; then additional sodium borohydride (9 g, 0.25 mole) is added, and the reaction is heated to reflux with stirring and maintained there for 7 hours. The reaction mixture is cooled to room temperature and water (100 ml) is added over a 1½-hour period. After stirring for 2 hours, the isopropanol is removed on a rotary evaporator, and the resulting paste slurried in water and extracted with diethyl ether. Evaporation of the ether layer gives the pyrazolidine as a viscous oil; 48.3 g, 72%, and analyzed as its HCl salt.

Analysis calculated for $C_{17}H_{21}N_2Cl$: C, 70.70; H, 7.33; N, 9.70. Found: C, 70.59; H, 7.49; N, 9.44.

A plurality of compounds set forth below in Table I, are prepared in a similar manner as described in Example 1 from pyrazolium quaternary salts and sodium borohyride.

EXAMPLE 2

Preparation of 1,2-Dimethyl-3-(m-fluorophenyl)-5-phenylpyrazolidine hydriodide

Sodium borohydride (76 g, 0.02 mole) is added to a slurry of 1,2-dimethyl-3-(m-fluorophenyl)-5-phenylpyrazolinium iodide (4 g, 0.01 mole) in isopropanol (125 ml). After becoming homogeneous, the reaction mixture is stirred for 24 hours. Water (10 ml) is then slowly added. Isopropanol is removed on a rotary evaporator and resultant residue is slurried in water (50 ml) and extracted with chloroform. Evaporation of the organic layer yields an oil, which is slurried in water. Aqueous hydriodic acid (5 ml, 46–50%) is next added. After stirring for one hour, resulting solid is filtered and dried to give 3,3 g, 83%; melting point 187°–189° C.

Analysis calculated for $C_{17}H_{20}N_2FI$: C, 51.27; H, 5.06; N, 7.03. Found: C, 51.59; H, 5.25; N, 7.10.

As stated in Table I below, several compounds are prepared as by utilizing the procedure of Example 2, namely, by the reduction of pyrazolinium salts with sodium borohydride.

EXAMPLE 3

An isomer mixture of 1,2-dimethyl-3,5-diphenyl-pyrazolidine (50 g, 80:20 cis:trans) as prepared in Example 1 above is taken up in a hexane-ether (80:20) mixture, and passed through a "dry" silica gel column 5 feet in length and 2½ inches in diameter with the same solvent system. The fractions are cut off, stripped off the silica gel with methanol, the methanol removed by evaporation and the residue azeotropically dried with toluene to yield:

(1) Faster moving trans-isomer >95%.

Analysis calculated for $C_{17}H_{20}N_2$: C, 80.91; H, 7.99; N, 11.10. Found: C, 80.92; H, 8.29; N, 10.91.

and (2) Slower cis-isomer >97%.

Analysis calculated for $C_{17}H_{20}N_2$: C, 80.91; H, 7.99; N, 11.10 Found: C, 80.52; H, 8.07; N, 10.90.

The hydrochlorides of each are prepared by adding aqueous hydrochloric acid (4 ml) to a water suspension of the appropriate cis-isomer, trans-isomer or cis-trans-isomer mixture. The cis-isomer (5.0 g) and the reaction mixture are stirred for ½ hour. The mixture is extracted with chloroform. The organic layer concentrated to an oil and azeotropically dried with toluene. The oil is taken up in chloroform (50 ml), and a solid precipitates out upon addition of ether, filtered and dried to yield 3.7 g, 65%; melting point 194°–195° C.

Analysis calculated for $C_{17}H_{21}N_2Cl$: C, 70.70; H, 7.33; N, 9.70. Found: C, 70.93; H, 7.48; N, 9.78.

EXAMPLE 4

The procedure of Example 1 is followed in every detail except that the pyrazolium salt corresponding to each of the compounds listed below and reported in Table I set forth is employed in lieu of 1,2-dimethyl-3,5-diphenylpyrazolium methyl sulfate.

(1) 1,2-Dimethyl-3,5-diphenylpyrazolidine hydrochloride (2) 1,2-Dimethyl-4-n-propoxy-3,5-diphenylpyrazolidine (3) 1,2-Dimethyl-4-n-propyl-3,5-diphenylpyrazolidine (4) 1,2-Dimethyl-4-propylthio-3,5-diphenylpyrazolidine (5) 1,2-Dimethyl-trans-3,5-diphenylpyrazolidine hydrochloride (6) 1,2-Dimethyl-4-methylthio-3,5-diphenylpyrazolidine (7) 3,5-Dicyclohexyl-1,2-dimethylpyrazolidine perchlorate (8) 3,5-Dicyclohexyl-1,2-dimethylpyrazolidine (9) 1,2-Dimethyl-3,5-diphenylpyrazolidine hydriodide

(10) 1,2-Dimethyl-3,5-diphenylpyrazolidine perchlorate

(11) 1,2-Dimethyl-3,5-diphenylpyrazolidine nitrate
(12) 1,2-Dimethyl-3,5-diphenylpyrazolidine hydrobromide
(13) 1,2-Dimethyl-3,5-diphenylpyrazolidine p-toluenesulfonate
(14) 1,2-Dimethyl-3,5-diphenylpyrazolidine sulfate
(15) 3-(p-Fluorophenyl)-1,2-dimethyl-5-phenylpyrazolidine hydriodide
(16) 3-(p-Fluorophenyl)-1,2-dimethyl-5-phenylpyrazolidine
(17) 3-(o-Fluorophenyl)-1,2-dimethyl-5-phenylpyrazolidine
(18) 3-(o-Fluorophenyl)-1,2-dimethyl-5-phenylpyrazolidine hydriodide
(19) 3-Cyclohexyl-1,2-dimethyl-5-phenylpyrazolidine hydriodide
(20) 1,2,4-Trimethyl-3,5-diphenylpyrazolidine hydriodide
(21) 4-Hydroxy-1,2-dimethyl-3,5-diphenylpyrazolidine
(22) 1,2-Dimethyl-3-(o-dimethylcarboxamidophenyl)-5-phenylpyrazolidine
(23) 3-(p-Chlorophenyl)-1,2-dimethyl-5-phenylpyrazolidine hydriodide
(24) 1,2-Dimethyl-3,5-di(o-tolyl) pyrazolidine hydriodide
(25) 4-Methoxy-1,2-dimethyl-3,5-diphenylpyrazolidine hydriodide
(26) 3-(m-Methoxyphenyl)-1,2-dimethyl-5-phenylpyrazolidine hydriodide
(27) 1,2-Dimethyl-3,5-[di(m-tolyl)]pyrazolidine hydriodide
(28) 1,2-Dimethyl-3-(o-tolyl)-5-(p-tolyl)pyrazolidine hydriodide
(29) 1,2-Dimethyl-3-(o-tolyl)-5-(p-tolyl)pyrazolidine
(30) 1,2-Dimethyl-3-(o-carbomethoxyphenyl)-5-phenylpyrazolidine
(31) 1,2-Dimethyl-3-(o-carboisopropyloxyphenyl)-5-phenylpyrazolidine

TABLE I

Preparation of Pyrazolidine Compounds having the Structure:

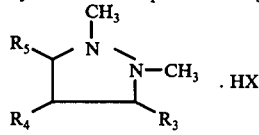

| No. | $R_3$ | $R_5$ | $R_4$ | HX | Melting Point °C | Method Employed | % Yield | Empirical Formula | Analyses Calculated | Found |
|---|---|---|---|---|---|---|---|---|---|---|
| 1 | Ph | Ph | H | HCl | 190–192 | Example 1 | 38–97 | $C_{17}H_{20}N_2 \cdot HCl$ | C, 70.70<br>H, 7.33<br>N, 9.70 | 70.59<br>7.49<br>9.54 |
| 2 | Ph | Ph | H | — | oil | Example 1 | 50–98 | $C_{17}H_{20}N_2$ | | |
| 3 | Ph trans | Ph trans | H | — | oil | Examples 1,3 | — | $C_{17}H_{20}N_2$ | C, 80.91<br>H, 7.99<br>N, 11.10 | 80.92<br>8.29<br>10.91 |
| 4 | Ph cis | Ph cis | H | — | oil | Examples 1,3 | — | $C_{17}H_{20}N_2$ | C, 80.91<br>H, 7.99<br>N, 11.10 | 80.91<br>8.07<br>10.90 |
| 5 | Ph trans | Ph trans | H | HCl | 152–154 | Examples 1,3 | 60 | $C_{17}H_{20}N_2 \cdot HCl$ | C, 70.70<br>H, 7.33<br>N, 9.70 | 68.58<br>7.22<br>9.36 |
| 6 | Ph cis | Ph cis | H | HCl | 194–195 | Examples 1,3 | 65 | $C_{17}H_{20}N_2 \cdot HCl$ | C, 70.70<br>H, 7.33<br>N, 9.70 | 70.93<br>7.48<br>9.78 |
| 7 | Cyclohexyl | Cyclohexyl | H | $HClO_4$ | 146–148 | Example 1 | 52 | $C_{17}H_{32}N_2 \cdot HClO_4$ | C, 55.95<br>H, 9.12<br>N, 7.68<br>Cl, 9.72 | 56.07<br>9.11<br>7.70<br>9.83 |
| 8 | Cyclohexyl | Cyclohexyl | H | — | oil | Example 1 | — | $C_{17}H_{32}N_2$ | | |
| 9 | Ph | Ph | H | HI | 195–196 | Example 1 | 69 | $C_{17}H_{20}N_2 \cdot HI$ | C, 53.70<br>H, 5.57<br>N, 7.37<br>I, 33.37 | 53.66<br>5.46<br>7.39<br>33.30 |
| 10 | Ph | Ph | H | $HClO_4$ | 138 | Example 1 | 66 | $C_{17}H_{20}N_2 \cdot HClO_4$ | C, 57.87<br>H, 6.00<br>N, 7.94<br>Cl, 10.05 | 57.98<br>5.95<br>7.87<br>10.24 |
| 11 | Ph | Ph | H | $HNO_3$ | 72–74 | Example 1 | 16 | $C_{17}H_{20}N_2 \cdot HNO_3$ | N, 13.32 | 13.16 |

TABLE I-continued

Preparation of Pyrazolidine Compounds having the Structure:

$$\begin{array}{c} CH_3 \\ | \\ R_5\phantom{xx}N \\ \phantom{xx}\diagdown\phantom{x}\diagdown \\ \phantom{xxxx}N-CH_3 \\ \phantom{xx}\diagup\phantom{x}\diagup \\ R_4\phantom{xxxx}R_3 \end{array} \cdot HX$$

| No. | $R_3$ | $R_5$ | $R_4$ | HX | Melting Point °C | Method Employed | % Yield | Empirical Formula | Analyses Calculated | Found |
|---|---|---|---|---|---|---|---|---|---|---|
| 12 | phenyl | phenyl | H | HBr | 196–199 | Example 1 | 60 | $C_{17}H_{20}N_2 \cdot$ HBr | C, 61.27<br>H, 6.35<br>N, 8.41<br>Br, 23.98 | 61.49<br>6.23<br>8.38<br>24.16 |
| 13 | phenyl | phenyl | H | $CH_3$-C$_6$H$_4$-SO$_3$H | viscous glass | Example 1 | 15 | $C_{17}H_{20}N_2 \cdot$ $C_7H_8SO_3$ | C, 66.34<br>N, 6.45<br>S, 7.38 | 65.52<br>6.20<br>7.06 |
| 14 | phenyl | phenyl | H | $H_2SO_4$ | 94 | Example 1 | 64 | $C_{17}H_{20}N_2 \cdot$ $H_2SO_4$ | N, 7.99 | 8.21 |
| 15 | phenyl | 4-F-phenyl | H | HI | 195–198 | Example 2 | — | $C_{17}H_{19}N_2F \cdot$ HI | C, 51.27<br>H, 5.06<br>N, 7.03 | 53.33<br>5.25<br>7.17 |
| 16 | phenyl | 4-F-phenyl | H | — | oil | Example 2 | 98 | $C_{17}H_{19}N_2F$ | C, 75.53<br>H, 7.08<br>N, 10.36 | 75.53<br>7.33<br>9.97 |
| 17 | phenyl | 2-F-phenyl | H | — | oil | Example 2 | >80 | $C_{17}H_{19}N_2F$ | C, 75.53<br>H, 7.08<br>N, 10.36 | 75.40<br>7.26<br>10.19 |
| 18 | phenyl | 2-F-phenyl | H | HI | 168–170 | Example 2 | — | $C_{17}H_{19}N_2F \cdot$ HI | C, 51.27<br>H, 5.06<br>N, 7.03 | 51.94<br>7.26<br>6.94 |
| 19 | phenyl | cyclohexyl | H | HI | 90 | Example 1 | — | $C_{17}H_{26}N_2 \cdot$ HI | H, 7.04<br>N, 7.29 | 6.78<br>6.98 |
| 20 | phenyl | phenyl | $CH_3$ | HI | 132–140 | Example 2 | 25 | $C_{18}H_{22}N_2 \cdot$ HI | C, 54.81<br>H, 5.88<br>N, 7.12 | 54.62<br>5.72<br>6.92 |
| 21 | phenyl | phenyl | OH | — | 87 | Example 1 | 64 | $C_{17}H_{20}N_2O$ | H, 7.51<br>N, 10.44 | 7.24<br>9.94 |
| 22 | phenyl | 3-F-phenyl | — | HI | 187–189 | Example 2 | 83 | $C_{17}H_{19}N_2F \cdot$ HI | C, 51.27<br>H, 5.06<br>N, 7.03 | 51.59<br>5.25<br>7.10 |
| 23 | phenyl | 4-Cl-phenyl | H | HI | 178 | Example 2 | 78 | $C_{17}H_{19}N_2Cl \cdot$ HI | C, 49.24<br>H, 4.86<br>N, 6.76 | 49.79<br>4.78<br>6.32 |
| 24 | 2-CH$_3$-phenyl | 2-CH$_3$-phenyl | H | HI | 212–219 | Example 2 | 86 | $C_{19}H_{24}N_2 \cdot$ HI | C, 55.89<br>H, 6.17<br>N, 6.86 | 56.36<br>6.22<br>6.73 |
| 25 | phenyl | phenyl | $OCH_3$ | HI $\cdot$ H$_2$O | 62–65 | Example 1 | 69 | $C_{18}H_{22}N_2O \cdot$ HI $\cdot$ H$_2$O | C, 50.47<br>H, 5.88<br>N, 6.54 | 50.88<br>5.09<br>6.54 |
| 26 | phenyl | 3-OCH$_3$-phenyl | H | HI | 113–116 | Example 2 | 63 | $C_{18}H_{22}N_2O \cdot$ HI | C, 52.69<br>H, 5.65<br>N, 6.83 | 54.33<br>5.93<br>6.94 |
| 27 | 3-CH$_3$-phenyl | 3-CH$_3$-phenyl | H | HI | 182–185 | Example 2 | 77 | $C_{19}H_{24}N_2 \cdot$ HI | C, 55.89<br>H, 6.17<br>N, 6.86 | 56.78<br>6.44<br>6.89 |
| 28 | 4-CH$_3$-phenyl | 2-CH$_3$-phenyl | H | HI | 167–168 | Example 2 | 52 | $C_{19}H_{24}N_2 \cdot$ HI | C, 55.89<br>H, 6.19<br>N, 6.86 | 56.03<br>6.19<br>6.80 |

TABLE I-continued

Preparation of Pyrazolidine Compounds having the Structure:

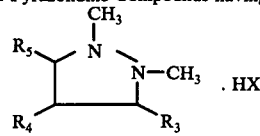

| No. | R$_3$ | R$_5$ | R$_4$ | HX | Melting Point °C | Method Employed | % Yield | Empirical Formula | Analyses Calculated | Found |
|---|---|---|---|---|---|---|---|---|---|---|
| 29 | CH$_3$-C$_6$H$_4$- | o-CH$_3$-C$_6$H$_4$- | H | — | oil | Example 2 | — | C$_{19}$H$_{24}$N$_2$ | C, 81.97<br>H, 7.97<br>N, 10.06 | 81.90<br>7.99<br>10.34 |
| 30 | cyclopropyl | phenyl | H | HI | 137–144 | Example 1 | 45 | C$_{14}$H$_{20}$N$_2$ · HI | C, 48.83<br>H, 6.15<br>N, 8.14 | 48.54<br>6.21<br>8.01 |
| 31 | phenyl | o-CO$_2$H-C$_6$H$_4$- | H | HI | 75–78 | Example 1* | 33 | C$_{18}$H$_{20}$N$_2$O$_2$ · HI | N, 6.60 | 5.87 |

*Compound 31 is prepared by a modified method of Ex. 1. The starting pyrazolium compound is 3-(o-carboxyphenyl) 1,2-dimethyl-5-phenylpyrazolium iodide, methyl ester, which after sodium borohydride reduction in isopropanol yields the pyrazolidine, but as a mixture of methyl and isopropyl esters of the carboxy function. This mixture is hydrolyzed by heating with 25% aqueous sodium hydroxide in methanol, and the product isolated with aqueous hydrogen iodide to afford the pyrazolidine hydroiodide.

EXAMPLE 5

The selective postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about 2 weeks. The test compounds are dispersed in 50/50 acetone/water mixtures containing 0.5% Tween® 20, a polyoxyethylene sorbitan monolaurate surfactant of Atlas Chemical Industries, (Wilmington, Delaware), in sufficient quantity to provide the equivalent of about 0.56 kg to 11.2 kgs. per hectare of active compound when applied to the plants through a spray nozzle operating at 40 psi for a predetermined time. After spraying, the plants are placed on greenhouse benches and are cared for in the usual manner, commensurate with conventional greenhouse practices. Two weeks after treatment, the seedling plants, with the exception of wild oats, are examined and evaluated according to the rating system provided below. Wild oats are rated at 5 weeks after treatment using the same system. The data obtained are reported in Table II below.

| Rating System: | % Difference in Growth from the Check* |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

*Based on visual determination of stand, size, vigor, chlorosis, growth malformation and over-all plant appearance.

Plant Abbreviations

LA - Lambsquarters (*Chenopodium album*)
MU - Mustard (*Brassica kaber*)
PI - Pigweed (*Amaranthus retroflexus*)
RW - Ragweed (*Ambrosia artemisiifolia*)
MG - Morningglory (*Ipomoea purpurea*)
BA - Barnyardgrass (*Echinochloa crusgalli*)
CR - Crabgrass (*Digitaria sanguinalis*)
FO - Green Foxtail (*Setaria viridis*)
WO - Wild Oats (*Avena fatua*)
VL - Velvetleaf (*Abutilon theophrasti*)

TABLE II

Postemergence Herbicidal Activity

| Structure | Treatment kg/ha | LA | MU | PI | RW | MG | BA | CR | FO | WO | VL |
|---|---|---|---|---|---|---|---|---|---|---|---|
| 1,2-Dimethyl-3,5-diphenylpyrazolidine hydrochloride* | 4.48 | | 9 | 9 | | 9 | 5 | 8 | 3 | 8 | 9 |
| | 2.24 | | 7 | 9 | | 7 | 0 | 6 | 1 | 7 | 8 |
| | 1.12 | | 8 | 8 | 0 | 2 | 0 | 1 | 1 | 6 | 5 |
| cis-trans mixture 1,2,4-Trimethyl-3,5-diphenylpyrazolidine hydrochloride | 11.2 | 9 | 9 | 8 | 0 | 5 | 8 | 5 | 2 | 8 | 9 |
| 1,2-Dimethyl-3-(o-tolyl)-5-(p-tolyl)-pyrazolidine hydriodide* | 10 | 9 | 6 | 9 | 3 | 2 | 3 | 6 | 2 | 8 | 8 |
| 1,2-Dimethyl-3-(o- | 11.2 | 9 | 9 | 9 | 9 | 3 | 6 | 8 | 9 | 8 | 8 |

TABLE II-continued

| | Postemergence Herbicidal Activity | | | | | | | | | | |
|---|---|---|---|---|---|---|---|---|---|---|---|
| | Treatment | | | | | Annual Weeds | | | | | |
| Structure | kg/ha | LA | MU | PI | RW | MG | BA | CR | FO | WO | VL |
| tolyl)-5-(p-tolyl)- | 4.48 | | 9 | 9 | | 9 | 2 | 5 | 2 | 7 | 7 |
| pyrazolidine | 1.12 | | 7 | 7 | | 5 | 2 | 3 | 1 | 7 | 7 |
| 1,2-Dimethyl-3-(o- | 11.2 | 9 | 9 | 7 | 0 | 3 | 5 | 8 | 7 | 8 | 9 |
| tolyl)-5-(p-tolyl)- | 4.48 | | 7 | 9 | | 9 | 3 | 3 | 7 | 6 | 8 |
| pyrazolidine hydriodide* | 1.12 | | 3 | 3 | | 0 | 1 | 0 | 2 | 7 | 5 |
| 3-(m-Fluorophenyl)-1,2-dimethyl-5-phenyl-pyrazolidine hydriodide* | 11.2 | 9 | 2 | 1 | 1 | 0 | 1 | 2 | 1 | 8 | 7 |
| 3-(p-Fluorophenyl)-1,2-dimethyl-5-phenyl-pyrazolidine hydriodide* | 11.2 | 9 | 9 | 9 | 0 | 2 | 1 | 2 | 0 | 9 | 9 |
| | 4.48 | | 7 | 8 | | 5 | 1 | 1 | 2 | 8 | 9 |
| 1,2-Dimethyl-3,5-diphenylpyrazolidine nitrate* | 4.48 | | 8 | 9 | | 8 | 2 | 2 | 1 | 9 | 6 |
| | 1.12 | | 3 | 6 | | 5 | 0 | 2 | 0 | 3 | 5 |
| 1,2-Dimethyl-3,5-diphenylpyrazolidine perchlorate* | 4.48 | | 9 | 9 | | 6 | 0 | 7 | 5 | 7 | 6 |
| | 1.12 | | 6 | 6 | | 1 | 0 | 5 | 0 | 7 | 6 |
| 1,2-Dimethyl-3,5-diphenylpyrazolidine hydriodide* | 4.48 | | 8 | 9 | | 5 | 3 | 7 | 5 | 5 | 8 |
| | 1.12 | | | | | | | | | 6 | |
| | 0.56 | | | | | | | | | 7 | |
| 3,5-Dicyclohexyl-1,2-dimethylpyrazolidine* | 4.48 | 9 | 9 | 9 | 5 | 9 | 7 | 8 | 3 | 7 | 9 |
| | 1.12 | 9 | 9 | 9 | 0 | 8 | 3 | 8 | 1 | 5 | 0 |
| | 0.56 | 7 | 7 | 0 | 0 | 1 | 0 | 7 | 0 | 1 | 0 |
| cis-1,2-Dimethyl-3,5-diphenylpyrazolidine | 11.2 | 9 | 9 | 9 | 0 | 2 | 3 | 1 | 3 | 7 | 9 |
| | 4.48 | | 9 | 9 | | 9 | 5 | 3 | 6 | 8 | 9 |
| | 1.12 | | 6 | 8 | | 7 | 0 | 2 | 1 | 8 | 6 |
| trans-1,2-Dimethyl-3,5-diphenylpyrazolidine | 4.48 | | 8 | 9 | | 6 | 3 | 3 | 0 | 5 | 7 |
| | 1.12 | | 1 | 5 | | 0 | 0 | 0 | 0 | 0 | 2 |
| 1,2-Dimethyl-3,5-diphenylpyrazolidine* | 4.48 | 0 | 9 | 7 | 2 | 0 | 0 | 0 | 1 | 7 | 6 |
| 3-(o-Fluorophenyl)-1,2-dimethyl-5-phenyl-pyrazolidine hydriodide* | 11.2 | 9 | 7 | 3 | 1 | 2 | 5 | 6 | 3 | 7 | 6 |
| 3-(o-Fluorophenyl)-1,2-dimethyl-5-phenyl-pyrazolidine* | 11.2 | 9 | 9 | 9 | 1 | 2 | 3 | 5 | 3 | 9 | 9 |
| 3-(p-Fluorophenyl)-1,2-dimethyl-5-phenyl-pyrazolidine* | 11.2 | 9 | 9 | 9 | 0 | 1 | 2 | 5 | 5 | 8 | 9 |
| | 4.48 | | 7 | 9 | | 5 | 2 | 3 | 2 | 8 | 6 |
| | 1.12 | | 5 | 0 | | 0 | 0 | 0 | 0 | 8 | 3 |
| 3,5-Dicyclohexyl-1,2-dimethylpyrazolidine perchlorate* | 10.0 | 8 | 8 | 7 | 2 | 5 | 2 | 7 | 2 | 9 | 5 |
| | 3.36 | 5 | 6 | 3 | 0 | 4 | 0 | 2 | 1 | 9 | 0 |
| trans-1,2-Dimethyl-3,5-diphenylpyrazolidine hydrochloride | 11.2 | 5 | 3 | 0 | 0 | 0 | 0 | 0 | 0 | 8 | 3 |
| 1,2-Dimethyl-3,5-diphenylpyrazolidine p-toluenesulfonate* | 4.48 | | 7 | 7 | | 6 | 1 | 5 | 0 | 8 | 6 |
| 1,2-Dimethyl-3,5-diphenylpyrazolidine hydrobromide* | 11.2 | 9 | 9 | 9 | 1 | 1 | 1 | 0 | 1 | 7 | 9 |
| | 4.48 | | 9 | 9 | | 7 | 1 | 7 | 1 | 5 | 7 |
| o-(1,2-Dimethyl-5-phenyl-pyrazolidin-3-yl) benzoic acid-, hydroiodide* | 11.2 | | 4 | 8 | 4 | 4 | 4 | 4 | 4 | 4 | 7 |

*cis-trans (80:20)

EXAMPLE 6

The preemergence activity of the compounds of the present invention is demonstrated by the following tests, wherein a 50/50 acetone/water mixture containing 0.5% v/v Tween ® 20 surfactant and sufficient test compound provide 11.2 kg per hectare of said compound when the mixture is applied to pots planted with seeds of test plant species.

The pots are prepared the day of herbicide treatment by putting 100 ml of soil in each plastic pot as a base. Seeds of test plant species are then separately mixed with soil, and 50 ml of the soil seed mix is added to the pot. Each of the weed species is contained in a separate pot. The pots are then tamped to level the soil. The soil is wetted with water prior to herbicide application to insure that the herbicide treatment solution spreads evenly over the surface of the pot. The pots are then arranged in 25.4 cm × 30.4 cm flats prior to chemical treatment.

The planted pots are treated with 5 ml of test solution and then placed on benches in the greenhouse. Pots are watered after treatment and held in the greenhouse for 3 weeks at which time the results are recorded, as reported below in Table III. The rating system used is described in Example 4 above.

TABLE III

| | Preemergence Herbicidal Activity | | | | | | | | | | |
|---|---|---|---|---|---|---|---|---|---|---|---|
| | Treatment | | | | | Annual Weeds | | | | | |
| Structure | kg/ha | LA | MU | PI | RW | MG | BA | CR | FO | WO | VL |
| 1,2-Dimethyl-3-(o-tolyl)-5-(p-tolyl)-pyrazolidine* | 11.2 | | 0 | 8 | 0 | 0 | 0 | 8 | 7 | 0 | 0 |
| 1,2-Dimethyl-3-(o- | 11.2 | | 0 | 9 | 0 | 0 | 0 | 9 | 9 | 2 | 8 |

TABLE III-continued

| | | Preemergence Herbicidal Activity | | | | | | | | | |
|---|---|---|---|---|---|---|---|---|---|---|---|
| Structure | Treatment kg/ha | LA | MU | PI | RW | MG | BA | CR | FO | WO | VL |
| tolyl)-5-(p-tolyl)-pyrazolidine hydriodide* | | | | | | | | | | | |
| 3,5-Dicyclohexyl-1,2-dimethylpyrazolidine perchlorate* | 11.2 | 8 | 2 | 3 | 0 | 0 | 2 | 0 | 0 | 4 | 2 |
| 1,2-Dimethyl-3,5-diphenylpyrazolidine hydriodide* | 11.2 | 7 | 0 | 8 | 0 | 0 | 0 | 0 | 7 | 4 | 7 |
| 3,5-Dicyclohexyl-1,2-diphenylpyrazolidine* | 11.2 | 8 | 4 | 7 | 0 | 2 | 8 | 9 | 8 | 8 | 4 |
| o-(1,2-Dimethyl-5-phenyl-pyrazolidin-3-yl) benzoic acid, hydroiodide* | 11.2 | | 8 | 9 | 9 | 4 | 8 | 9 | 9 | 7 | 9 |
| 3-Cyclopropyl-1,2-dimethyl-5-phenylpyrazolidine hydroiodide* | 10.0 | | 7 | 8 | 0 | 0 | 0 | 0 | 8 | 3 | 9 |

*cis-trans (80:20)

EXAMPLE 7

The selective postemergence effectiveness of the compounds of the present invention for controlling wild oats in the presence of wheat is demonstrated by the following tests. In these tests, seedlings of wild oats and several varieties of wheat, growing in separate pots, are sprayed with solutions or suspensions of test compound dispersed in a 50/50 acetone/water mixture in sufficient quantity to provide the equivalent of about 0.56 kg to 4.48 kg per hectare of active compound when applied to the plants through a spray nozzle operating at 40 psi for a predetermined time. All spray solutions contain 0.5% Tween ® 20, a polyoxyethylene sorbitan monolaurate surfactant. Two or three replicates per treatment are used. After spraying, the plants are placed on greenhouse benches and cared for in the usual manner, commensurate with conventional greenhouse practices. Five weeks after treatment, the seedling plants are examined and evaluated according to the rating system described in Example 5. Data obtained are reported in Table IV below and show that the pyrazolidines I and pyrazolidine salts II of the subject invention are highly wheat selective.

Wheat varieties employed in these tests include: Waldron, Lark, Bonanza, Olaf, Genesee and Era.

TABLE IV

| | | Postemergence Wild Oat Control in the Presence of Wheat | | | | | | | | | | | | | | | | | |
|---|---|---|---|---|---|---|---|---|---|---|---|---|---|---|---|---|---|---|---|
| | Rate | Wheat Varieties | | | | | | | | | | | | | | | | | |
| Compound | kg/ha | Waldron | | Lark | | Bonanza | | Olaf | | Genesee | | Era | | | Wild Oats | | | | |
| 1,2-Dimethyl-3,5-diphenylpyrazolidine hydrochloride* | 1.12 | 2 | 2 | 1 | 1 | 1 | 1 | 0 | 0 | 0 | 0 | 0 | 0 | | 7 | 6 | 6 | | |
| | 0.56 | 1 | 0 | 0 | 1 | 0 | 1 | 0 | 0 | 0 | 0 | | | | 3 | 2 | 3 | | |
| 3,5-Dicyclohexyl-1,2-dimethylpyrazolidine* | 4.48 | | | 0 | 0 | 0 | 0 | 1 | 0 | | | 0 | 0 | 0 | 8 | 6 | 7 | | |
| cis-1,2-Dimethyl-3,5-diphenylpyrazolidine | 0.56 | | | 0 | 0 | 0 | 0 | 0 | 0 | | | 0 | 0 | 0 | 7 | 8 | 8 | | |
| 1,2-Dimethyl-3,5-diphenylpyrazolidine perchlorate* | 4.48 | | | 5 | 8 | 6 | 5 | 5 | 5 | | | 0 | 0 | 0 | 8 | 7 | 7 | | |
| | 1.12 | | | 0 | 2 | 0 | 0 | 0 | 0 | | | 0 | 0 | 0 | 8 | 8 | 7 | | |
| | 0.56 | | | 0 | 0 | 0 | 0 | 0 | 0 | | | 0 | 0 | 0 | 2 | 6 | 6 | | |
| 1,2-Dimethyl-3,5-diphenylpyrazolidine nitrate* | 4.48 | | | 3 | 5 | 3 | 3 | 2 | 2 | | | 0 | 0 | 0 | 6 | 8 | 7 | | |
| | 1.12 | | | 0 | 0 | 0 | 0 | 0 | 0 | | | 0 | 0 | 0 | 3 | 6 | 3 | | |
| 1,2-Dimethyl-3,5-diphenylpyrazolidine hydrobromide* | 4.48 | | | 6 | 7 | 6 | 5 | 5 | 6 | | | 0 | 0 | 0 | 8 | 7 | 2 | | |
| | 1.12 | | | 0 | 0 | 0 | 1 | 1 | 1 | | | 0 | 0 | 0 | 8 | 8 | 8 | | |
| 1,2-Dimethyl-3,5-diphenylpyrazolidine hydriodide* | 4.48 | | | 0 | 2 | 1 | 0 | 2 | 0 | | | 0 | 0 | 0 | 7 | 3 | 5 | | |
| | 1.12 | | | 0 | 0 | 0 | 0 | 0 | 0 | | | 0 | 0 | 0 | 7 | 8 | 7 | | |
| | 0.56 | | | 0 | 0 | 0 | 0 | 0 | 0 | | | 0 | 0 | 0 | 3 | 6 | 6 | | |
| 3,5-Dicyclohexyl-1,2-dimethylpyrazolidine perchlorate* | 4.48 | | | 0 | 0 | 0 | 0 | 0 | 0 | | | 0 | 0 | 0 | 7 | 7 | 7 | | |
| cis-trans mixture of 1,2,4-Trimethyl-3,5-diphenyl-pyrazolidine hydriodide | 4.48 | | | 5 | 5 | 3 | 5 | 5 | 5 | | | 0 | 0 | 0 | 8 | 8 | 8 | | |
| | 1.12 | | | 1 | 5 | 3 | 3 | 5 | 5 | | | 0 | 0 | 0 | 7 | 7 | 8 | | |
| | 0.56 | | | 1 | 1 | 1 | 1 | 1 | 0 | | | 0 | 0 | 0 | 6 | 7 | 7 | | |
| 3-Cyclohexyl-1,2-dimethyl-5-phenyl-pyrazolidine* | 4.48 | | | 2 | 1 | 1 | 0 | 0 | 0 | | | 0 | 0 | 0 | 7 | 7 | 6 | | |
| | 1.12 | | | 0 | 0 | 0 | 0 | 0 | 0 | | | 0 | 0 | 0 | 7 | 2 | 6 | | |
| 3-(m-Fluorophenyl)-1,2-dimethyl-5-phenyl-pyrazolidine hydriodide* | 1.12 | | | 0 | 0 | 0 | 0 | 0 | 0 | | | 0 | 0 | 0 | 5 | 8 | 3 | | |
| 3-(p-Fluorophenyl)-1,2-dimethyl-5-phenyl-pyrazolidine hydriodide* | 4.48 | | | 5 | 5 | 2 | 1 | 3 | 1 | | | 0 | 0 | 0 | 7 | 6 | 8 | | |
| | 1.18 | | | 0 | 0 | 0 | 0 | 0 | 0 | | | 0 | 0 | 0 | 8 | 7 | 7 | | |
| | 0.56 | | | 0 | 0 | 0 | 0 | 0 | 0 | | | 0 | 0 | 0 | 6 | 6 | 7 | | |
| 3-(o-Fluorophenyl)-1,2-dimethyl-5-phenyl-pyrazolidine* | 4.48 | | | 5 | 5 | 3 | 7 | 5 | 3 | | | 0 | 0 | 0 | 9 | 8 | 8 | | |
| | 1.18 | | | 3 | 5 | 5 | 5 | 6 | 5 | | | 0 | 0 | 0 | 7 | 7 | 8 | | |
| | 0.56 | | | 0 | 0 | 1 | 1 | 0 | 0 | | | 0 | 0 | 0 | 7 | 5 | 7 | | |
| 1,2-Dimethyl-3,5-diphenylpyrazolidine* | 4.48 | | | 3 | 3 | 5 | 2 | 0 | 1 | | | 0 | 0 | 0 | 8 | 7 | 7 | | |

*cis-trans (80:20)

EXAMPLE 8

The postemergence control of wild oats with the compounds of the present invention is further demonstrated in the following tests. The procedure employed and the rating system used is the same as described above in Example 7. The plant species employed in these tests is wild oats (*Avena fatua*). Two replicates per treatment are used.

Data obtained are reported in Table V below.

TABLE V

| Postemergence Control of Wild Oats | | |
|---|---|---|
| Compound | Rate kg/ha | Wild Oats |
| 3-(p-Fluorophenyl)- | 4.48 | 8 8 |
| 1,2-dimethyl-5-phenyl- | 1.12 | 8 8 |
| pyrazolidine* | 0.56 | 6 6 |
| 3-(p-Fluorophenyl)- | 4.48 | 8 8 |
| 1,2-dimethyl-5-phenyl- | 1.12 | 8 7 |
| pyrazolidine hydriodide* | 0.56 | 3 7 |
| 1,2-Dimethyl-3-(o- | 4.48 | 6 5 |
| tolyl)-5-(p-tolyl)- | 1.12 | 7 8 |
| pyrazolidine hydriodide* | 0.56 | 6 3 |
| 1,2-Dimethyl-3-(o- | 4.48 | 8 7 |
| tolyl)-5-(p-tolyl)- | 1.12 | 6 7 |
| pyrazolidine* | 0.56 | 7 7 |

*cis-trans (80:20)

We claim:

1. A process for the preparation of a pyrazolidine compound which comprises the step of: reducing at temperatures ranging from room temperature to reflux temperatures in the presence of a molar excess of sodium borohydride dissolved in a lower monohydric alcohol, a compound defined as follows:

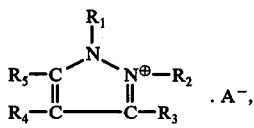

wherein $R_1$ and $R_2$ each represent alkyl $C_1$-$C_4$; $R_3$ and $R_5$ each represent members selected from the group consisting of cycloalkyl $C_3$-$C_7$, methylcycloalkyl $C_4$-$C_8$, cycloalkenyl $C_3$-$C_7$, benzyl, alkyl $C_2$-$C_{12}$ and

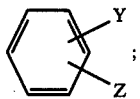

Y and Z each represent members selected from the group consisting of hydrogen, halogen, alkyl $C_1$-$C_4$, alkoxy $C_1$-$C_4$ and carboxyl, $R_4$ represents a member selected from the group consisting of hydrogen, alkyl $C_1$-$C_{10}$ and alkoxy $C_1$-$C_4$, provided when $R_4$ is hydrogen or methyl, at least one of $R_3$ and $R_5$ is a member other than phenyl; and A is an anion, and thereafter recovering resultant pyrazolidine compound.

2. The process according to claim 1 wherein sodium borohydride in isopropanol is employed to attain said reduction.

3. A process for the preparation of a pyrazolidine compound which comprises the steps of: reducing at room temperature in the presence of a molar excess of sodium borohydride dissolved in a lower monohydric alcohol, a compound selected from the group consisting of:

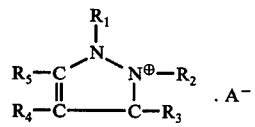

and

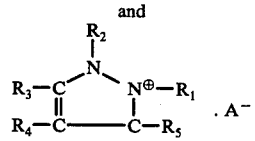

wherein $R_1$ and $R_2$ each represent alkyl $C_1$-$C_4$; $R_3$ and $R_5$ each represent members selected from the group consisting of cycloalkyl $C_3$-$C_7$, methylcycloalkyl $C_4$-$C_8$, cycloalkenyl $C_3$-$C_7$, benzyl, alkyl $C_2$-$C_{12}$ and

Y and Z each represent members selected from the group consisting of hydrogen, halogen, alkyl $C_1$-$C_4$, alkoxy $C_1$-$C_4$ and carboxyl, $R_4$ represents a member selected from the group consisting of hydrogen, alkyl $C_1$-$C_{10}$ and alkoxy $C_1$-$C_4$, provided when $R_4$ is hydrogen or methyl, at least one of $R_3$ and $R_5$ is a member other than phenyl; and A is an anion, and thereafter recovering resultant pyrazolidine compound.

4. The process according to claim 3 wherein sodium borohydride in isopropanol is employed.

* * * * *